US011503680B2

(12) United States Patent
Kimsey-Lin

(10) Patent No.: US 11,503,680 B2
(45) Date of Patent: Nov. 15, 2022

(54) SYSTEMS AND METHODS FOR OPERATING A LIGHT SYSTEM

(71) Applicant: The Boeing Company, Chicago, IL (US)

(72) Inventor: Melanie L. Kimsey-Lin, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 17/095,365

(22) Filed: Nov. 11, 2020

(65) Prior Publication Data

US 2021/0063891 A1 Mar. 4, 2021

Related U.S. Application Data

(63) Continuation of application No. 16/267,367, filed on Feb. 4, 2019, now Pat. No. 10,852,638, which is a
(Continued)

(51) Int. Cl.
*A61L 2/10* (2006.01)
*H05B 45/00* (2022.01)
(Continued)

(52) U.S. Cl.
CPC .............. *H05B 45/00* (2020.01); *A61L 2/10* (2013.01); *A61L 2/24* (2013.01); *B82Y 10/00* (2013.01);
(Continued)

(58) Field of Classification Search
CPC .......... A61L 2/10; A61L 2/24; A61L 2202/11; A61L 2202/14
(Continued)

(56) References Cited

U.S. PATENT DOCUMENTS 5,483,127 A 1/1996 Widmayer
5,768,853 A * 6/1998 Bushnell .................. A23L 3/28
53/167
(Continued)

FOREIGN PATENT DOCUMENTS

CA 2777014 4/2011
CA 2904971 7/2016
(Continued)

OTHER PUBLICATIONS

Buonanno, M., Ponnaiya, B., Welch, D., Stanislauskas, M., Randers-Pehrson, G., Smilenov, L., . . . & Brenner, D. J. (2017). Germicidal efficacy and mammalian skin safety of 222-nm UV light. Radiation research, 187(4), 493-501 (Year: 2017).*
(Continued)

*Primary Examiner* — Wyatt A Stoffa
(74) *Attorney, Agent, or Firm* — McDonnell Boehnen Hulbert & Berghoff LLP

(57) ABSTRACT

In an example, a method of operating an ultraviolet (UV) light source includes providing a supply power to the UV light source, and activating, using the supply power, the UV light source to emit UV light during a series of activation cycles. The method also includes, during at least one activation cycle in the series, sensing the UV light emitted by the UV light source to measure an optical parameter of the UV light. The optical parameter is related to an antimicrobial efficacy of the UV light. The method further includes adjusting, based on the measured optical parameter, an electrical parameter of the supply power to maintain a target antimicrobial efficacy of the UV light over the series of activation cycles.

20 Claims, 9 Drawing Sheets

Related U.S. Application Data continuation of application No. 15/632,968, filed on Jun. 26, 2017, now Pat. No. 10,228,622.

(51) Int. Cl.
| | | |
|---|---|---|
| *A61L 2/24* | (2006.01) | |
| *H05B 45/37* | (2020.01) | |
| *B82Y 10/00* | (2011.01) | |
| *G03F 7/20* | (2006.01) | |
| *H01J 61/80* | (2006.01) | |
| *H05B 41/32* | (2006.01) | |
| *H05G 2/00* | (2006.01) | |
| *H05H 1/04* | (2006.01) | |
| *H05B 41/36* | (2006.01) | |
| *H05B 45/10* | (2020.01) | |
| *H05B 45/325* | (2020.01) | |
| *H05B 45/355* | (2020.01) | |

(52) U.S. Cl.
CPC ...... *G03F 7/70033* (2013.01); *G03F 7/70525* (2013.01); *H01J 61/80* (2013.01); *H05B 41/32* (2013.01); *H05B 45/37* (2020.01); *H05G 2/005* (2013.01); *H05H 1/04* (2013.01); *A61L 2202/11* (2013.01); *A61L 2202/14* (2013.01); *H05B 41/36* (2013.01); *H05B 45/10* (2020.01); *H05B 45/325* (2020.01); *H05B 45/355* (2020.01)

(58) Field of Classification Search
USPC ..................................................... 250/504 R
See application file for complete search history.

(56) References Cited

U.S. PATENT DOCUMENTS

| | | | |
|---|---|---|---|
| 6,512,234 B1 | 1/2003 | Sasges et al. | |
| 6,877,248 B1 | 4/2005 | Cross et al. | |
| 8,033,686 B2* | 10/2011 | Recker | H05B 47/28 362/249.02 |
| 8,084,752 B2 | 12/2011 | Ranta et al. | |
| 8,138,690 B2 | 3/2012 | Chemel et al. | |
| 8,339,069 B2 | 12/2012 | Chemel et al. | |
| 8,368,321 B2 | 2/2013 | Chemel et al. | |
| 8,543,249 B2 | 9/2013 | Chemel et al. | |
| 8,552,664 B2 | 10/2013 | Chemel et al. | |
| 8,593,135 B2 | 11/2013 | Chemel et al. | |
| 8,805,550 B2 | 8/2014 | Chemel et al. | |
| 8,954,170 B2 | 2/2015 | Chemel et al. | |
| 9,623,133 B2* | 4/2017 | Childress | H05B 47/115 |
| 9,700,072 B2* | 7/2017 | Dobrinsky | A23L 3/28 |
| 9,783,974 B1 | 10/2017 | Tillotson | |
| 9,855,353 B1 | 1/2018 | Stacy | |
| 9,993,571 B2 | 6/2018 | Lin et al. | |
| 10,130,727 B1 | 11/2018 | Byrnes et al. | |
| 10,145,055 B1 | 12/2018 | Harlan et al. | |
| 10,228,622 B2* | 3/2019 | Kimsey-Lin | H05B 45/00 |
| 10,272,169 B2 | 4/2019 | Lin et al. | |
| 10,363,329 B2* | 7/2019 | Childress | B64F 5/30 |
| 10,852,638 B2* | 12/2020 | Kimsey-Lin | H05B 41/32 |
| 2006/0163135 A1 | 7/2006 | Ellis et al. | |
| 2009/0218512 A1* | 9/2009 | Ranta | A61L 2/24 250/455.11 |
| 2010/0193629 A1 | 8/2010 | Breit et al. | |
| 2011/0057123 A1 | 3/2011 | Ho | |
| 2011/0155915 A1 | 6/2011 | Brueck et al. | |
| 2012/0235050 A1 | 9/2012 | Abe et al. | |
| 2013/0330235 A1 | 12/2013 | Stibich et al. | |
| 2014/0059796 A1* | 3/2014 | Boodaghians | B64D 11/00 250/455.11 |
| 2014/0266695 A1 | 9/2014 | Addison et al. | |
| 2015/0086420 A1* | 3/2015 | Trapani | A61L 9/20 422/24 |
| 2015/0343104 A1* | 12/2015 | Maxik | G01J 1/42 250/201.1 |
| 2016/0088868 A1 | 3/2016 | Dobrinsky et al. | |
| 2016/0195427 A1 | 7/2016 | Vance et al. | |
| 2016/0220716 A1 | 8/2016 | Childress et al. | |
| 2016/0250362 A1 | 9/2016 | Mackin | |
| 2016/0317690 A1* | 11/2016 | Dayton | A61L 2/10 |
| 2017/0049915 A1* | 2/2017 | Brais | H05B 47/115 |
| 2017/0107659 A1 | 4/2017 | Hills | |
| 2017/0283062 A1 | 10/2017 | Childress | |
| 2017/0283092 A1 | 10/2017 | Brown et al. | |
| 2017/0284076 A1 | 10/2017 | Jensen | |
| 2018/0050122 A1 | 2/2018 | Lin et al. | |
| 2018/0051447 A1 | 2/2018 | Hills et al. | |
| 2018/0055964 A1* | 3/2018 | Dayton | A61L 2/00 |
| 2018/0064833 A1 | 3/2018 | Childress et al. | |
| 2018/0079528 A1 | 3/2018 | Siegmeth et al. | |
| 2018/0084956 A1 | 3/2018 | Childress | |
| 2018/0117190 A1* | 5/2018 | Bailey | H05B 45/12 |
| 2018/0193501 A1* | 7/2018 | Ufkes | A61L 2/10 |
| 2018/0369434 A1 | 12/2018 | Callahan | |
| 2018/0369435 A1* | 12/2018 | Dhiman | G01J 1/0228 |
| 2018/0369439 A1 | 12/2018 | Brockschmidt et al. | |
| 2018/0371733 A1 | 12/2018 | Childress et al. | |
| 2018/0373157 A1 | 12/2018 | Kimsey-Lin | |
| 2019/0171111 A1 | 6/2019 | Kimsey-Lin | |
| 2020/0179544 A1* | 6/2020 | Ufkes | H05B 47/125 |
| 2021/0052758 A1* | 2/2021 | Brais | A61L 2/10 |

FOREIGN PATENT DOCUMENTS

| | | |
|---|---|---|
| JP | H09-253083 A | 9/1997 |
| JP | 2002263645 | 9/2002 |
| JP | 2012-192381 A | 10/2012 |
| JP | 2013-538066 A | 10/2013 |
| WO | 99/62567 | 12/1999 |

OTHER PUBLICATIONS

Summons to attend Oral Proceedings Pursuant to Rule 115(1) EPC, issued by the European Patent Office in Application No. EP 18 172 464.2 dated Mar. 16, 2021.
Office Action issued by the Canadian Patent Office in application No. 3,006,530 dated Jul. 7, 2021.
First Office Action issued by the Chinese Patent Office in application No. 2018106327886 dated Jul. 5, 2021.
European Search Report and Written Opinion issued by the European Patent Office in European Patent Application No. 18172464.2, dated Nov. 19, 2018 (7 pages).
Preliminary Office Action issued by the Brazilian Patent Office in application No. BR102018013043-9 dated May 2, 2022.

\* cited by examiner

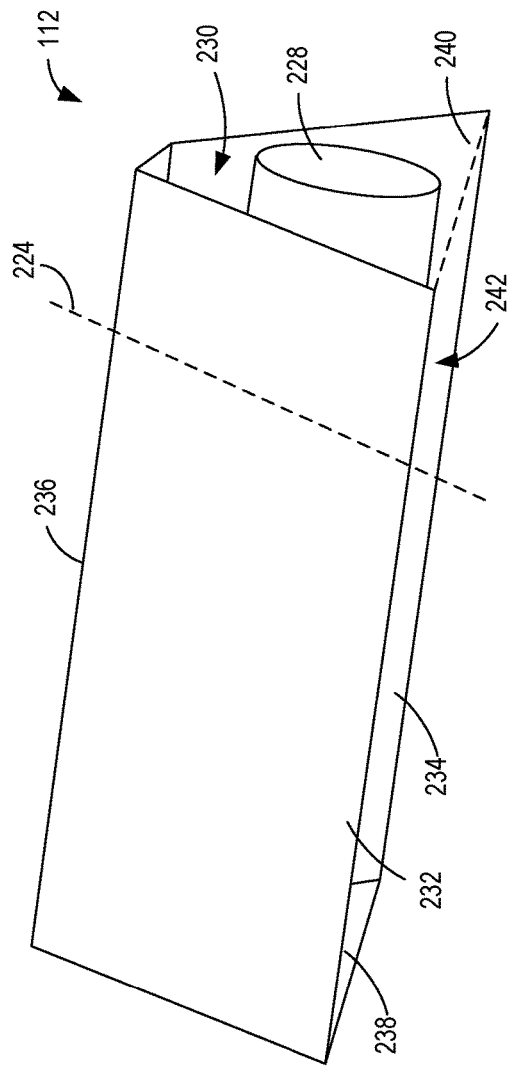
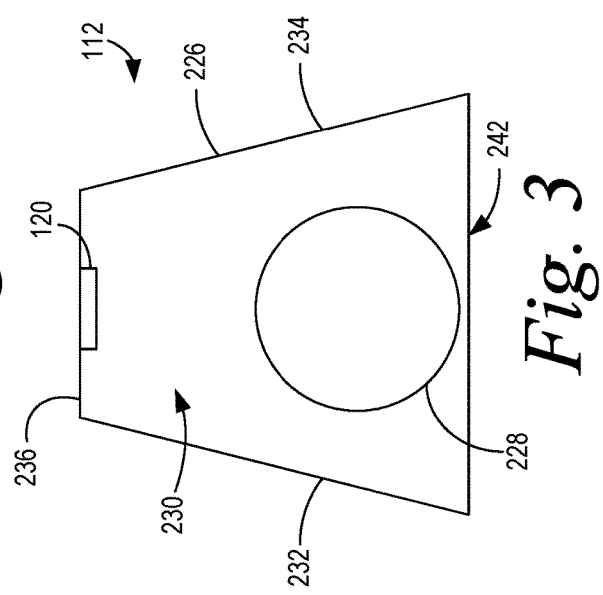

SYSTEMS AND METHODS FOR OPERATING A LIGHT SYSTEM

CROSS-REFERENCE TO RELATED APPLICATION

The present application is a continuation of U.S. patent application Ser. No. 16/267,367, filed on Feb. 4, 2019, which is a continuation of U.S. patent application Ser. No. 15/632,968, filed on Jun. 26, 2017, the contents of which are hereby incorporated by reference in their entirety.

FIELD

The present disclosure generally relates to systems and methods for light systems, and more particularly to systems and methods for operating an ultraviolet (UV) light source to disinfect an environment.

BACKGROUND

Pathogens may be spread between humans, between animals, or between humans and animals in many different ways. Consequently, there is an increasing need for the disinfection of public environments. One approach for disinfecting an environment involves irradiating the environment with ultraviolet (UV) light using a UV light source.

SUMMARY

In an example, a method of operating a UV light source is described. The method includes providing a supply power to the UV light source and activating, using the supply power, the UV light source to emit UV light during a series of activation cycles. The method also includes, during at least one activation cycle in the series, sensing the UV light emitted by the UV light source to measure an optical parameter of the UV light. The optical parameter is related to an antimicrobial efficacy of the UV light. The method further includes adjusting, based on the measured optical parameter, an electrical parameter of the supply power to maintain a target antimicrobial efficacy of the UV light over the series of activation cycles.

In another example, a light control system is described. The light control system includes a power converter configured to convert an input power received from a power source to a supply power. The supply power has an electrical parameter that is adjustable by the power converter. The light control system also includes a UV light source configured to receive the supply power and emit UV light during a series of activation cycles. An intensity of the UV light emitted by the UV light source is based, at least in part, on the electrical parameter of the supply power. The light control system further includes a light sensor configured to measure an optical parameter of the UV light emitted by the UV light source. The optical parameter is related to an antimicrobial efficacy of the UV light.

Additionally, the light control system includes a control device communicatively coupled to the power converter and the light sensor. The control device is configured to maintain a target antimicrobial efficacy of the UV light by iteratively performing a plurality of acts including: (i) receiving, from the light sensor, a sensor signal indicating the optical parameter measured by the light sensor, (ii) performing a comparison of the optical parameter indicated by the sensor signal to a target optical parameter, and (iii) based on the comparison, providing a feedback signal to the power converter to cause the power converter to adjust the electrical parameter of the supply power for a next activation cycle in the series.

In another example, a method of operating a UV light source is described. The method includes receiving an input power from a power source and performing, using the input power and the UV light source, a series of activation cycles to disinfect an environment. Each activation cycle includes converting the input power to a supply power. An electrical parameter of the supply power is adjustable, and the electrical parameter has a baseline value for an initial activation cycle in the series. Each activation cycle also includes activating, using the supply power, the UV light source to emit UV light, sensing the UV light emitted by the UV light source to measure an optical parameter of the UV light, and comparing the measured optical parameter to a target optical parameter. The target optical parameter is related to a target antimicrobial efficacy of the UV light. Each activation cycle further includes deciding, based on the comparison, whether to adjust the electrical parameter for a next activation cycle in the series or maintain the electrical parameter for the next activation cycle.

For each activation cycle, if the decision is to adjust the electrical parameter, then the method includes adjusting the electrical parameter for the next activation cycle to adjust the antimicrobial efficacy of the UV light for the next activation cycle, and if the decision is to maintain the electrical parameter, then the method includes maintaining the electrical parameter for the next activation cycle. For at least one activation cycle in the series, the decision is to adjust the electrical parameter.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

FIG. 2 illustrates a perspective view of a UV light source according to an example embodiment.

FIG. 3 illustrates a cross-sectional view of the UV light source shown in FIG. 2.

DETAILED DESCRIPTION

Figure 1:
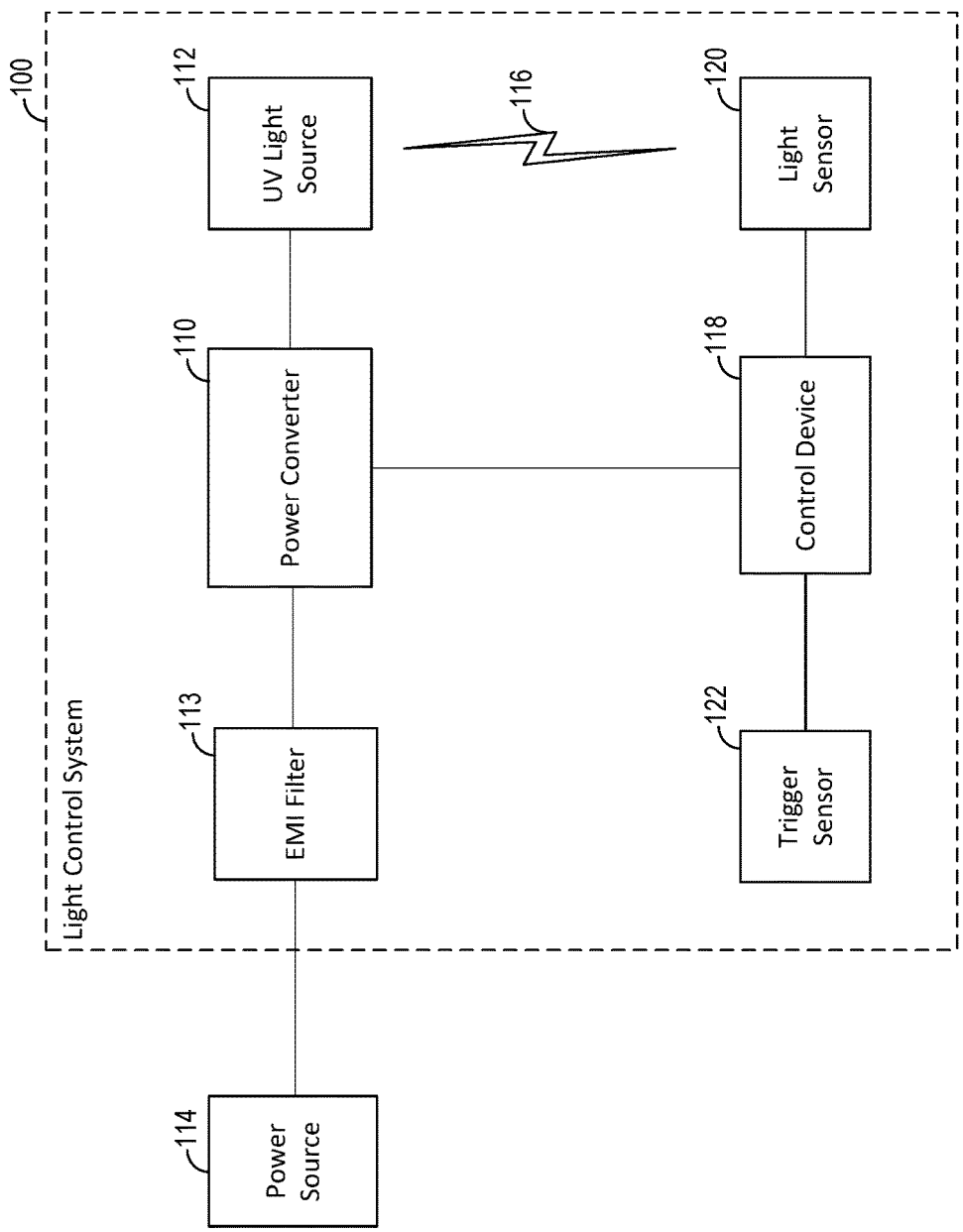
FIG. 1 illustrates a simplified block diagram of a light control system according to an example embodiment.

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

The systems and methods of the present disclosure provide light control systems and methods for operating a UV light source to maintain a target level of antimicrobial efficacy over a series of activation cycles. When activated during each activation cycle, the UV light source emits UV light, which can kill and/or disable microorganisms such as bacteria, viruses, molds, and/or other pathogens. For example, when microorganisms are exposed to a sufficiently high dose of UV light, the UV light can damage nucleic acids and/or disrupt the deoxyribonucleic acid (DNA) of the microorganisms, rendering the microorganisms unable to carry out cellular functions and infect people.

The antimicrobial efficacy of the UV light during the activation cycle is related to factors such as, for instance, the length of time a microorganism is exposed to the UV light (i.e., the "exposure time"), the intensity of the UV light, and the wavelength of the UV light. As one example, the antimicrobial efficacy of the UV light at a particular wavelength can be specified as a UV dose, which can be determined based on an equation having the general form of:

$$\text{UV dose} = \text{UV light intensity} \times \text{exposure time} \qquad (\text{eq. 1})$$

where the UV dose is specified in $mWs/cm^2$, the UV light intensity is specified in $\mu W/cm^2$ at a predetermined distance (e.g., one meter) from the UV light source, and the exposure time is specified in seconds.

Over time, the intensity of the UV light emitted by the UV light source declines due to, for example, lamp lumen depreciation (LLD) and/or lamp dirt depreciation (LDD). For instance, LLD can be caused by chemical reactions, which can deposit light-absorbing particles within the UV light source, over multiple activation cycles. Whereas, LDD can be caused by an accumulation of debris (e.g., dirt and/or dust particles) on an exterior surface of the UV light source, which block UV light emission.

Additionally, for example, the intensity of the UV light emitted by the UV light source can be affected by the temperature of the UV light source. For instance, the temperature of the UV light source can vary due to changes in an ambient temperature of an environment in which the UV light source is operating, and/or due to heat resulting from operation of the UV light source itself. Accordingly, because the intensity of the UV light source changes over multiple activation cycles, it can be challenging to maintain the target level of antimicrobial efficacy throughout the life of the UV light source.

The example systems and methods described herein can beneficially overcome challenges to operating a UV light source at a target level of antimicrobial efficacy over multiple activation cycles and/or the life of the UV light source. In particular, the systems and methods can dynamically adjust an electrical parameter of a supply power provided to the UV light source to compensate for changes in the intensity of the UV light over a series of activation cycles.

Within examples, a light control system can include a power converter, a UV light source, a light sensor, and a control device. The power converter can provide a supply power to the UV light source, which the UV light source can use to emit UV light during a series of activation cycles. The light sensor can sense the emitted UV light and measure an optical parameter, which is related to the antimicrobial efficacy of the UV light. For instance, the light sensor can measure an irradiance of the UV light. Based on the measured optical parameter, the control device can cause the power converter to dynamically adjust an electrical parameter of the supply power to maintain the target antimicrobial efficacy of the UV light over the series of activation cycles.

In some implementations, the control device can cause the power converter to increase a frequency and/or a wattage of the supply power to increase the intensity of the UV light emitted by the UV light source. This can help to compensate for reduced efficiencies of the UV light source due to, for example, LLD, LDD, and/or temperature variations. In additional or alternative implementations, the control device can cause the power converter to decrease the frequency and/or wattage of the supply power to decrease the intensity of the UV light emitted by the UV light source. This can be beneficial, for example, to compensate for temperature variations and/or prior overcorrections to the frequency and/or wattage of the supply power. Additionally, for example, decreasing the intensity of the UV light can beneficially facilitate extending the useful life of the UV light source. In this way, the cost of operating the light control system can be reduced (or minimized) as a lamp of the UV light source may need to be replaced and/or serviced less frequently than conventional systems.

In one example, the target level of antimicrobial efficacy is a UV dose of approximately 10 $mWs/cm^2$. In additional or alternative examples, the target level of antimicrobial efficacy can be a UV dose between approximately 2 $mWs/cm^2$ and approximately 500 $mWs/cm^2$. Different microorganisms may have different abilities to withstand exposure to the UV light. In some implementations, the target level of antimicrobial efficacy can be based on a target microorganism-kill rate for one or more types of microorganisms that are targeted for disinfection by the light control system. As an example, the targeted micro-organism kill rate can be approximately 80% to approximately 99.99%. For instance, the targeted microorganism-kill rate can be approximately 80%, approximately 90%, approximately 95%, approximately 99%, approximately 99.9%, and/or approximately 99.99% of the one or more target microorganisms irradiated by the UV dose.

Within examples, the light control system described herein can be located in any environment, which can benefit from disinfection. For instance, the light control system can be in a vehicle (e.g., an aircraft, a boat, a train, and/or an automobile), a medical environment (e.g., a hospital, a doctor office, and/or other healthcare facility), a restaurant, an office, and/or a household. In one implementation, the light control system can be located in a lavatory of a vehicle (e.g., a lavatory of an aircraft).

Referring now to FIG. 1, a light control system 100 is depicted according to an example embodiment. As shown in FIG. 1, the light control system 100 includes a power converter 110 coupled to a UV light source 112. The power converter 110 can also be coupled to a power source 114 via an electromagnetic interference (EMI) filter 113. The EMI filter 113 can suppress EMI conducted between the light control system 100 and the power source 114 (and/or other electronic systems in an environment in which the light control system 100 is located).

The power converter 110 receives an input power from the power source. As an example, the power source 114 can provide the input power as an alternating current (AC) power. In one implementation, the power source 114 can provide the input power as a three-phase AC power with a voltage of 115 volts (V) and a frequency of approximately 360 Hertz (Hz) to approximately 800 Hz. For instance, in a vehicle, the power source 114 can include an engine turbine that generates electrical energy and an electrical distribution system that provides the generated electrical energy to the light control system 100 in the form of the input power. Other example power sources 114 are also possible.

The power converter 110 converts the input power to the supply power 114 and outputs the supply power to the UV light source 112. Within examples, the supply power can have a different AC waveform than the input power. That is, a value of the electrical parameter of the supply power can be different than a value of the electrical parameter of the input power. As examples, the electrical parameter can be a frequency, a voltage, a current, and/or a wattage of the AC waveform of the input power and the supply power. An example power converter 110 for converting the input power to the supply power is described further below with respect to FIG. 4.

The UV light source 112 receives the supply power from the power converter 110. When activated during an activation cycle, the UV light source 112 can use the supply power to emit UV light 116 at an intensity and/or for an exposure time (i.e., at a level of antimicrobial efficacy), which are based on the supply power received by the UV light source 112 during the activation cycle. As described in detail below, the power converter 110 can dynamically adjust the electrical parameter of the supply power to facilitate the UV light source 112 emitting the UV light at a target level of antimicrobial efficacy over a series of activation cycles.

Within examples, the light source 112 can be configured to emit the UV light 116 in a range between a minimum intensity and a maximum intensity based, at least in part, on the electrical parameter of the supply power. As also described in detail below, for an initial activation cycle, the electrical parameter can have a baseline value such that the UV light source 112 emits the UV light 116 at an intensity that (i) is less than the maximum intensity of the UV light source 112 and (ii) provides the target antimicrobial efficacy. Then, for one or more activation cycles after the initial activation cycle, the electrical parameter can have an adjusted value (which is different than the baseline value) to maintain the target level of antimicrobial efficacy. In this way, the light control system 100 can compensate for depreciating antimicrobial efficacy of the UV light source 112 due to (i) aging of the UV light source 112, (ii) a temperature of the UV light source 112, (iii) an accumulation of debris on a surface of the UV light source 112, (iv) an increased distance between the UV light source 112 and a target surface, and/or (v) a reduced exposure time.

As examples, the UV light source 112 can include one or more excimer bulbs, mercury-vapor lamps, and/or light emitting diodes (LEDs). More generally, the UV light source 112 can be a light source that emits the UV light 116 at a wavelength within the UV spectrum (i.e., between approximately 10 nanometers (nm) and approximately 400 nm). In some implementations, the UV light source 112 can be a light source that emits UV light 116 at a wavelength within the far-UV spectrum (e.g., between approximately 190 nm and approximately 240 nm). For instance, in one implementation, the UV light source 112 can be a light source that emits the UV light 116 at a wavelength of approximately 222 nm. By emitting the UV light 116 at a wavelength in the far-UV spectrum, the UV light source 112 can more rapidly disinfect the environment than by emitting the UV light 116 at other wavelengths in the UV spectrum. One example UV light source 112 is further described below with respect to FIGS. 2-3.

As also shown in FIG. 1, the light control system 100 can also include a control device 118 communicatively coupled to the power converter 110 and a light sensor 120. The light sensor 120 can sense the UV light 116 emitted by the UV light source 112, measure an optical parameter of the sensed UV light 116, and provide a sensor signal to the control device 118 indicating the optical parameter measured by the light sensor 120. Accordingly, the light sensor 120 can be positioned such that a portion of the UV light 116 emitted by the light source 112 is incident on the light sensor 120. As examples, the light sensor 120 can include one or more photodiodes, photojunction devices, light dependent resistors (LDRs), and/or photoconductive cells to sense and measure the optical parameter of the UV light 116. In an additional or alternative example, the light sensor 120 can include a filter to facilitate the light sensor 120 measuring the UV light 116 at a specific wavelength related to the target antimicrobial efficacy.

The control device 118 can receive the sensor signal from the light sensor 120, and compare the optical parameter indicated by the sensor signal to a target optical parameter. Based on the comparison, the control device 118 can provide a feedback signal to the power converter 110 to cause the power converter 110 to adjust the electrical parameter of the supply power.

The optical parameter measured by the light sensor 120 is related to the antimicrobial efficacy of the UV light 116 emitted by the UV light source 112 during the activation cycle, and the target optical parameter is related to the target antimicrobial efficacy of the UV light 116. For example, the optical parameter of the UV light 116 measured by the light sensor 120 can be an irradiance of the UV light 116, and the target optical parameter can be an expected irradiance and/or a range of expected irradiances for the UV light 116 at the target antimicrobial efficacy. The control device 118 can thus compare the irradiance indicated by the sensor signal to the expected irradiance(s) and, based on the comparison, the control device 118 can decide whether to adjust the electrical parameter for the next activation cycle in the series or maintain the electrical parameter for the next activation cycle in the series. In this example, the electrical parameter can be the frequency and/or wattage of the supply power.

In one implementation, when the control device 118 determines that the irradiance indicated by the sensor signal is equal to the expected irradiance(s), the control device 118 can decide to maintain the frequency and/or wattage of the supply power for the next activation cycle. Additionally or alternatively, when the control device 118 determines that the irradiance indicated by the sensor signal is less than the expected irradiance(s), the control device 118 can decide to adjust the frequency and/or wattage of the supply power and provide the feedback signal to the power converter 110 to cause the power converter 110 to increase the frequency and/or wattage of the supply power. By increasing the frequency and/or wattage of the supply power, the UV light source 112 can emit the UV light 116 at an increased intensity during the next activation cycle.

Also, additionally or alternatively, when the control device 118 determines that the irradiance indicated by the sensor signal is greater than the expected irradiance(s), the control device 118 can decide to adjust the frequency and/or wattage of the supply power and provide the feedback signal to the power converter 110 to cause the power converter to decrease the frequency and/or wattage of the supply power. By decreasing the frequency and/or wattage of the supply power, the UV light source 112 can emit the UV light 116 at a decreased intensity during the next activation cycle.

In this way, when the UV light 116 emitted by the light source 112 varies over time due to aging and/or environmental factors, the control device 118 and the light sensor 120 can dynamically adjust operation of the power converter 110 to maintain the target level of antimicrobial efficacy over a plurality of activation cycles of the UV light source 112 (e.g., over the life of the UV light source 112).

In FIG. 1, the control device 118 can also control activating and deactivating the UV light source 112. For example, the control device 118 can be coupled to one or more trigger sensors 122 that can detect one or more trigger conditions and responsively generate a trigger-sensor signal indicating that the trigger condition(s) were detected. The control device 118 can (i) receive the trigger-sensor signal indicating that the trigger condition was detected, (ii) determine, based on the trigger-sensor signal, that one or more criteria are met, and (iii) responsive to the determination that the one or more criteria are met, transmit a control signal to activate the UV light source 112.

In an example, the trigger sensor(s) 122 can include a motion sensor, an occupancy sensor, a thermal sensor, an open/close sensor, an infrared sensor device, an ultrasonic sensor device, a floor pressure sensor, and/or other types of sensors. For instance, in an example in which the light control system 100 is located on a vehicle having a lavatory, the trigger condition(s) detected by the trigger sensor(s) 122 can include a door of the lavatory being opened, the door of the lavatory being closed, the lavatory being occupied, and/or the lavatory being unoccupied. Additionally, for example, the one or more criteria that is used by the control device 118 to determine whether to activate the UV light source 112 can include one or more criterion such as a door of the lavatory being closed, the lavatory being unoccupied, the lavatory having been occupied a predetermined number of times since a pervious activation of the UV light source 112, and/or a predetermined amount of time having passed since the previous activation cycle of the UV light source 112.

In general, the control device 118 is a computing device that is configured to control operation of the light control system 100. As such, the control device 118 can be implemented using hardware, software, and/or firmware. For example, the control device 118 can include one or more processors and a non-transitory computer readable medium (e.g., volatile and/or non-volatile memory) that stores machine language instructions or other executable instructions. The instructions, when executed by the one or more processors, cause the light control system 100 to carry out the various operations described herein. The control device 118, thus, can receive data (including data indicated by the sensor signals and/or trigger-sensor signals) and store the data in memory as well.

Referring now to FIGS. 2-3, the UV light source 112 is depicted according to an example embodiment. In particular, FIG. 2 depicts a perspective view of the UV light source 112 and FIG. 3 depicts a cross-sectional view of the UV light source 112 taken through the line 224 shown in FIG. 2.

As shown in FIGS. 2-3, the UV light source 112 includes a housing 226 and a lamp 228. In an example, the lamp 228 can include one or more gas discharge light bulbs and/or LEDs that emit the UV light 116 when activated using the supply power. The housing 226 can define an interior space 230. For example, in FIGS. 2-3, the housing 226 includes a first side-wall 232, a second side-wall 234, and a top wall 236 extending between the first side-wall 232 and the second side-wall 234. The housing 226 also includes a first end wall 238 and a second end wall 240. In FIG. 2, the second end wall 240 is depicted in broken lines to better show the lamp 228 in the housing 226. The first side-wall 232, the second side-wall 234, the top wall 236, the first end wall 238, and the second end wall 240 define the interior space 230.

The housing 226 also includes an aperture 242 defined by the first side-wall 232, the second side-wall 234, the first end wall 238, and the second end wall 240 at a bottom of the housing 226. In an alternative example, the housing 226 can have a bottom wall made of a transparent material (e.g., quartz) instead of the aperture 242. Also, in additional or alternative examples, the housing 226 can have a greater or lesser quantity of walls 232, 234, 236, 238, 240 and/or the housing 226 can have a different shape and/or size than the housing 226 depicted in FIGS. 2-3.

The lamp 228 is in the interior space 230 of the housing 226. For example, the lamp 228 can be coupled to the first end wall 238 and the second end wall 240 of the housing 226. With the lamp 228 in the interior space 230, the housing 226 can protect the lamp 228 against dirt, dust, and/or impacts. Additionally, for example, the housing 226 can include a reflective material (e.g., polished aluminum) on one or more interior surfaces of the housing 226 to direct a greater amount of the UV light 116 through the aperture 242 and thereby increase (or maximize) the efficiency of the UV light source 112.

As shown in FIGS. 2-3, the light sensor 120 is also in the interior space 230 of the housing 226. For example, the light sensor 120 can be coupled to the top wall 236 in one implementation. In this location, the light sensor 120 can sense the UV light 116 emitted by the UV light source 112 as described above. By locating the light sensor 120 in the interior space 230 of the housing 226, there can be a reduced risk of interference and/or damage to the light sensor 120. For example, locating the light sensor 120 in the interior space 230 of the housing 226 can mitigate dust and dirt accumulating on the light sensor 120 and interfering with the light sensor 120 sensing the UV light 116.

Because the distance between the light sensor 120 and the lamp 228 may be different than the distance between the lamp 228 and a target surface or object to be irradiated and disinfected by the UV light 116, the optical parameter of the UV light 116 measured by the light sensor 120 may differ from the optical parameter of the UV light 116 incident on the target surface or object. In such a scenario, the control device 118 can take the difference in distance into account when performing the comparison of the optical parameter indicated by the sensor signal and the target optical parameter, and deciding whether to adjust or maintain the electrical parameter for the next activation cycle.

Although the light sensor 120 is coupled to the top wall 236 in FIGS. 2-3, the light sensor 120 can be at a different location in the housing 226 in additional or alternative examples. Further still, the light sensor 120 can be at a location external to the housing 226 in additional or alternative examples. For instance, the light sensor 120 can be located at the target surface or object to be disinfected. This location can obviate the control device 118 taking into account differences in the distance between the lamp 228, the light sensor 120, and the target surface or object to be disinfected.

Also, although a single light sensor 120 is depicted in FIGS. 2-3, the light control system 100 can include more than one light sensor 120 in additional or alternative examples. For instance, the control device 118 can receive a respective sensor signal from each light sensor 120 and average the measured optical parameter values. This may provide the light control system 100 with redundancy in the event of one of the light sensors 120 experiencing an operational transient.

Figure 4:
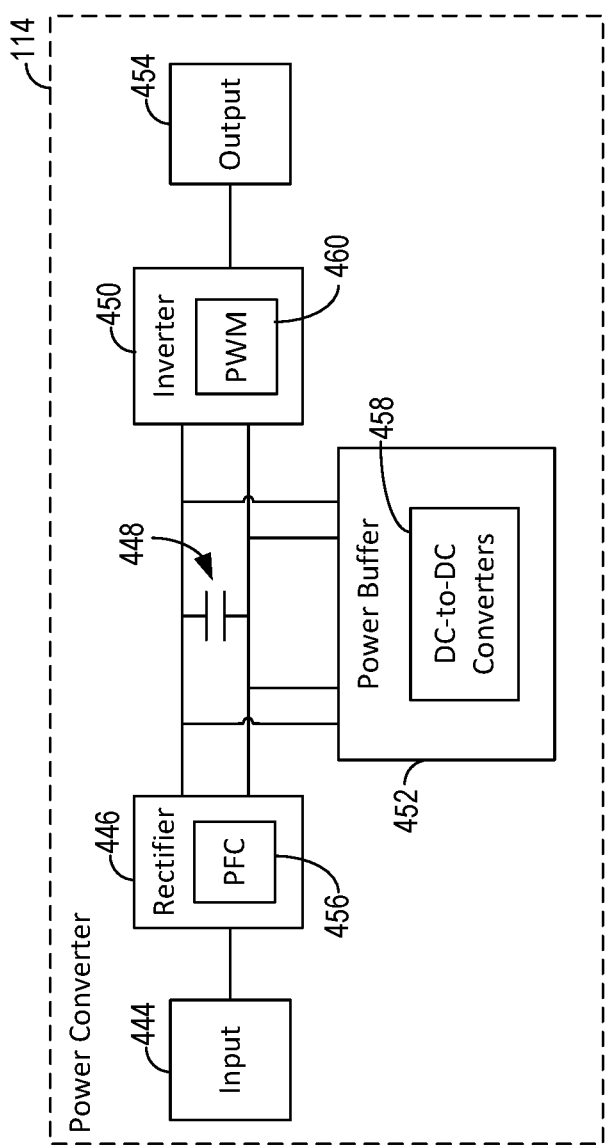
FIG. 4 illustrates a simplified block diagram of a power converter according to an example embodiment.

Referring now to FIG. 4, the power converter 110 is depicted according to an example embodiment. As shown in FIG. 4, the power converter 110 includes the input 444, a rectifier 446, a direct current (DC) link 448, an inverter 450, a power buffer 452, and an output 454. The input 444 receives the input power from the power source 114. The rectifier 446 is coupled to and receives the input power from the input 444. The rectifier 446 can convert the AC input power into a DC power. In an example, the rectifier 446 include a power factor corrector (PFC) 456 that corrects a power factor of the input power to facilitate more efficient use of the input power by the light control system 100. The PFC 456 can also facilitate isolating the light control system 100 from the power source 114 (and/or other electrical subsystems coupled to the power source 114). Within examples, the PFC 456 can include a passive PFC circuit, an active PFC circuit, and/or a dynamic PFC circuit.

The rectifier 446 is coupled to the inverter 450 via the DC link 448. When the light source 112 is activated, the inverter 450 converts the DC power received from the rectifier 446 into an AC power, which provides a portion of the supply power at the output 454. The DC link 448 facilitates the coupling of the rectifier 446 and the inverter 450. In one example, the DC link 448 can include a capacitor coupled in parallel between the rectifier 446 and the inverter 450. The DC link 448 can assist in mitigating transients propagating toward the power source 114 and/or assist in smoothing pulses in the rectified DC power provided by the rectifier 446.

As shown in FIG. 4, the power buffer 452 is coupled in parallel between the rectifier 446 and the DC link 448, and between the DC link 448 and the inverter 450. The power buffer 452 stores power using the input power received at the input 444 when the UV light source 112 deactivated. As examples, the power buffer 452 can include a battery, a capacitor, and/or another type of energy storage device.

In the example of FIG. 4, the power buffer 452 includes a plurality of DC-to-DC converters 458 coupled to each other. When the UV light source 112 is deactivated, the DC-to-DC converters 458 receive the DC power from the rectifier 446. In one implementation, the DC-to-DC converters 458 include a first DC-to-DC converter that steps down the DC power received from the rectifier 446 and a second DC-to-DC converter that steps up the DC power. This configuration of the DC-to-DC converters 458 can beneficially reduce (or minimize) the size and/or weight of the power buffer 452.

As noted above, the inverter 450 is coupled to the rectifier 446 and the power buffer 452. In this arrangement, when the light source 112 is activated, the inverter 450 can receive the DC power from the rectifier 446 and the power stored in the power buffer 452. The inverter 450 can convert this combination of DC power from the rectifier 446 and the power buffer 452 into the supply power, which has an AC waveform. In an example, the inverter 450 can include a pulse-width modulator (PWM) 460, which can switch on and off to control a frequency and/or wattage of the supply power. In another example, the inverter 450 can additionally or alternatively include a sine wave generator and/or a carrier wave generator to convert the combination of DC power to the supply power.

As noted above, the control device 118 can provide the feedback signal to adjust the electrical parameter of the supply power. In an example, the electrical parameter can be the frequency and/or the wattage of the AC waveform of the supply power, and the feedback signal can thus cause the PWM 460 to switch of and off with a frequency and/or pulse width based on the feedback signal to adjust the frequency and/or the wattage of the supply power.

The power converter 110 depicted in FIG. 4 can facilitate activating the UV light source 112 in an scenario in which the input power has a low wattage relative to a power requirement of the UV light source 112. For example, the power converter 110 can receive, at the input 444, the input power from the power source 114 during a first portion of a time interval and a second portion of the time interval. The UV light source 112 is deactivated during the first portion of the time interval. The UV light source 112 is activated during the second portion of the time interval. However, the input power received during the second portion of the time interval is insufficient by itself for the UV light source 112 to emit the UV light 116 at the intensity providing the target level of antimicrobial efficacy for a given activation cycle.

To address this limitation of the input power, the power converter 110 can store the input power in the power buffer 452 during the first portion of the time interval. Later, during the second portion of the time interval, the power converter 110 can provide to the UV light source 112 the supply power that combines (i) the input power received at the input 444 during the second portion of the time interval and (ii) the power stored in the power buffer 452 during the first portion of the time interval. The combination of power is sufficient for activating the UV light source 112 to emit the UV light 116 at the target level of antimicrobial efficacy.

In one example, the target level of antimicrobial efficacy can be defined by an intensity of 1 $\mu W/cm^2$ intensity and an exposure time of 10 seconds. In this example, the input 444 can receives the input power as a three-phase AC power with a voltage of approximately 115 $V_{AC}$, a frequency of approximately 400 Hz, and a current of 0.5 Amps (A) such that the input power has a wattage of approximately 100 W (i.e., less than 1 kW). As such, the input power is insufficient by itself to activate the UV light source 112 at the target level of antimicrobial efficacy. The rectifier 446 can convert the input power to the DC power having a voltage of approximately 200 $V_{DC}$ and a current of approximately 0.5 A. The power buffer 452 can include a first DC-to-DC converter that steps down the DC power from 200 $V_{DC}$ to 28 $V_{DC}$, and a second DC-to-DC converter that steps the DC power from 28 $V_{DC}$ to 200 $V_{DC}$.

In this arrangement, during the first portion of the time interval, the rectifier 446 converts the input power to the 200 $V_{DC}$ power and the power buffer 452 stores the 200 $V_{DC}$ power. During the second portion of the time interval, the rectifier 446 converts the input power to the 200 $V_{DC}$ power and provides the 200 $V_{DC}$ power to the inverter 450. Also, during the second portion of the time interval, the power buffer 452 provides the stored power to the inverter 450 with a voltage of approximately 200 $V_{DC}$ and a current of approximately 5 A. As a result, the inverter 450 receives the combination of power at 200 $V_{DC}$ and a current of at least 5 A such that the supply power has a wattage equal to or greater than 1 kW. In this example, the power buffer 452 can have an energy storage capacity at least large enough to provide the stored power at 200 $V_{DC}$ and 5 A for the 10 second exposure time. In this way, the power converter 110 can provide the UV light source 112 with sufficient power to achieve the target level of antimicrobial efficacy during the activation cycle of the UV light source 112.

In the example described above, the power stored in the power buffer 452 provides approximately 90% of the supply power and the input power received during the second portion of the time interval provides approximately 10% of the supply power. In additional or alternative examples, the input power received during the second portion of time can provide approximately 5% to approximately 95% of the supply power and the power stored in the power buffer 452 can provide the remainder of the supply power.

Although the power converter 110 can beneficially overcome challenges to operating the UV light source 112 at the target level of antimicrobial efficacy in a limited-power environment, the power converter 110 can omit the power buffer 452 in alternative examples in which the input power is not limited relative to the power requirements of the UV light source 112. Omitting the power buffer 452 can beneficially further reduce the weight and/or size of the power converter 452.

In operation, the light control system 100 can perform a series of activation cycles to disinfect an environment with the UV light 116 at the target antimicrobial efficacy. During each activation cycle in the series, the power converter 110 receives the input power from the power source 114 and converts the input power to the supply power. For example, in FIG. 4, the power converter 110 can (i) receive the input power at the input 444, (ii) convert the input power to the supply power using the rectifier 446, the inverter 450, and/or the power buffer 452, and (iii) output the supply power at the output 454.

Also, during each activation cycle, the UV light source 112 uses the supply power to emit the UV light 116. The antimicrobial efficacy of the UV light 116 emitted by the UV light source 112 is based, at least in part, on the electrical parameter of the supply power. For instance, for each activation cycle, the intensity of the UV light 116 emitted by the light source 112 can be based on the frequency and/or wattage of the supply power provided to the UV light source 112 by the power converter 110 during the activation cycle. As described above, the electrical parameter is adjustable by the power converter 110 (e.g., using the PWM 460 to control the frequency and/or pulse width of the supply power).

For an initial activation cycle in the series, the electrical parameter has the baseline value. Accordingly, for the initial activation cycle in the series, the power converter 110 converts the input power to the supply power by outputting the supply power with the electrical parameter at the baseline value. As an example, the power converter 110 can switch the PWM 460 on and off to provide a frequency and/or pulse width corresponding to the baseline value.

As noted above, the baseline value is such that the UV light source 112 emits the UV light 116 at an intensity that (i) is less than the maximum intensity of the UV light source 112 and (ii) provides the target antimicrobial efficacy during the initial activation cycle. By setting the electrical parameter to the baseline value, the light control system 100 allows for the electrical parameter and thus the intensity of the UV light 116 to be increased during subsequent activation cycles. Additionally, for example, by setting the electrical parameter to the baseline value, the life of the UV light source 112 can be extended.

Also, during the initial activation cycle, the light sensor 120 senses the UV light 116 emitted by the UV light source 112, measures the optical parameter of the UV light 116, and transmits the sensor signal indicating the measured optical parameter to the control device 118. For example, the light sensor 120 can measure the irradiance of the UV light 116 and transmit the sensor signal indicating the irradiance to the control device 118.

The control device 118 receives the sensor signal, and compares the measured optical parameter to the target optical parameter. Based on the comparison, the control device 118 decides whether to adjust the electrical parameter for a next activation cycle in the series or maintain the electrical parameter for the next activation cycle. Responsive to the control decision deciding to maintain the electrical parameter, the control device 118 can transmit the feedback signal to cause the power converter 110 to maintain the value of electrical parameter for the next activation cycle or the control device 118 can forgo transmitting the feedback signal to the power converter 110.

Whereas, responsive to the control device 118 deciding to adjust the electrical parameter, the control device 118 transmits the feedback signal to the power converter 110 to adjust the electrical parameter for the next activation cycle. Based on the feedback signal, the power converter 110 adjusts the electrical parameter from the baseline value to an adjusted value, which is different than the baseline value. As described above, based on the comparison of the measured optical parameter and the target optical parameter, the control device 118 can cause the power converter 110 to increase and/or decrease the antimicrobial efficacy of the UV light for the next activation cycle. For example, the control device 118 can cause the power converter 110 to adjust the electrical parameter to compensate for depreciating antimicrobial efficacy of the UV light source 112 due to (i) aging of the lamp 228 of the UV light source 112, (ii) a temperature of the UV light source 112, (iii) an accumulation of debris on a surface of the UV light source 112, (iv) an increased distance between the UV light source 112 and a target surface, and/or (v) a reduced exposure time.

After the initial activation cycle, the control system 100 can perform the remaining activation cycles in the series. During each of the remaining activation cycles, the control system 100 can repeat the process described above of converting the input power to the supply power, activating the UV light source using the supply power, measuring the optical parameter of the emitted UV light, and adjusting and/or maintaining the electrical parameter. In this way, the light control system 100 can iteratively adjust and/or maintain the value of the electrical parameter over the series of activation cycles to maintain the target level of antimicrobial efficacy.

In the example operation described above, the light sensor 120 senses the UV light 116 to measure the optical parameter and the control device 118 decides whether to adjust the electrical parameter during each activation cycle in the series. In an alternative example, the light sensor 120 senses the UV light 116 to measure the optical parameter and the control device 118 decides whether to adjust the electrical parameter once every N activation cycles, where N is an integer value that is greater than or equal to two. In an alternative example, the light sensor 120 senses the UV light 116 to measure the optical parameter and the control device 118 decides whether to adjust the electrical parameter once every N activation cycles, where N is an integer value that is greater than or equal to two. In another additional or alternative example, In an alternative example, the light sensor 120 senses the UV light 116 to measure the optical parameter and the control device 118 decides whether to adjust the electrical parameter on a periodic basis (e.g., once every M minutes, where M is an integer value).

Also, in the example operation described above, the light sensor 120 senses the UV light 116 to measure the optical parameter and the control device 118 decides whether to adjust the electrical parameter during the initial activation cycle in the series. In an alternative example, the light sensor 120 can sense the UV light 116 to measure the optical parameter and the control device 118 decides whether to adjust the electrical parameter starting with a different activation cycle in the series.

Figure 5:
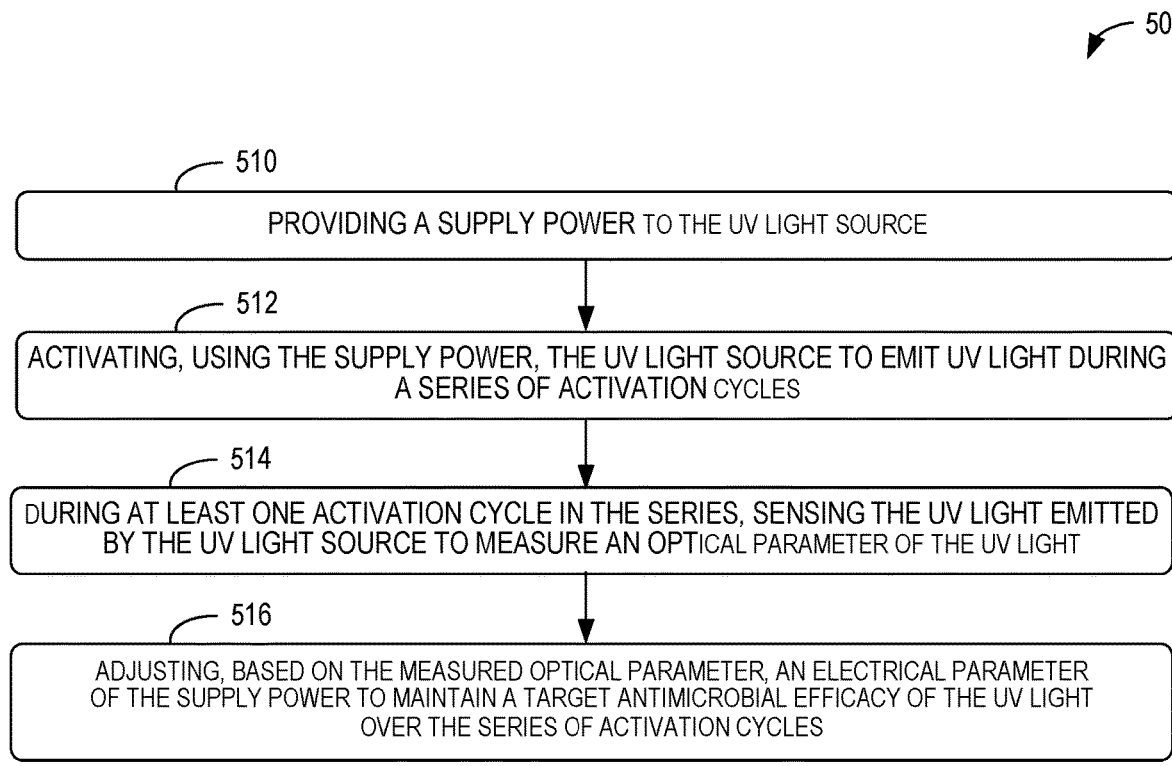
FIG. 5 illustrates a flow chart of an example process for operating a UV light source according to an example embodiment.

Referring now to FIG. 5, a flowchart for a process 500 of operating a UV light source is illustrated according to an example embodiment. As shown in FIG. 5, at block 510, the process 500 includes providing a supply power to the UV light source. At block 512, the process 500 includes activating, using the supply power, the UV light source to emit UV light during a series of activation cycles. At block 514, the process 500 includes, during at least one activation cycle in the series, sensing the UV light emitted by the UV light source to measure an optical parameter of the UV light. The optical parameter is related to an antimicrobial efficacy of the UV light. At block 516, the process 500 includes adjusting, based on the measured optical parameter, an electrical parameter of the supply power to maintain a target antimicrobial efficacy of the UV light over the series of activation cycles.

Figure 6:
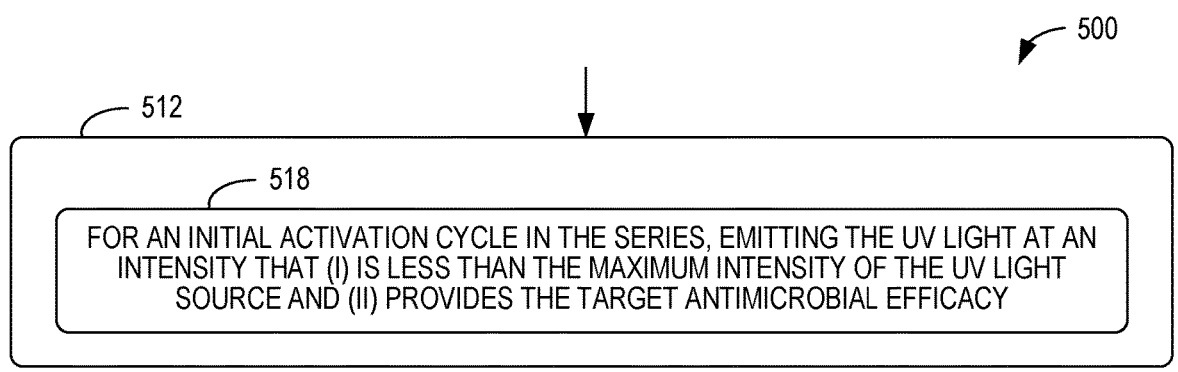
FIG. 6 illustrates a flow chart of an example process for operating a UV light source that can be used with the process shown in FIG. 5.

FIGS. 6-12 depict additional aspects of the process 500 according to further examples. In an example, the UV light source can be configured to emit the UV light in a range between a minimum intensity and a maximum intensity. As shown in FIG. 6, for an initial activation cycle in the series, the electrical parameter has a baseline value such that activating the UV light source using the supply power at block 512 includes emitting the UV light at an intensity that (i) is less than the maximum intensity of the UV light source and (ii) provides the target antimicrobial efficacy at block 518.

Figure 7:
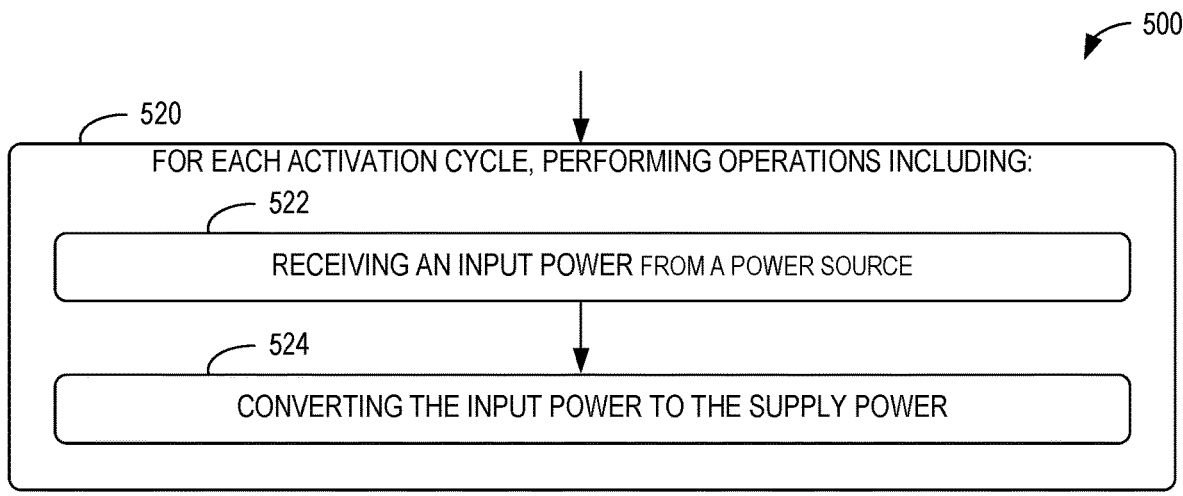
FIG. 7 illustrates a flow chart of an example process for operating a UV light source that can be used with the process shown in FIG. 6.

As shown in FIG. 7, the process 500 can also include, for each activation cycle in the series, performing operations at block 520. For example, at block 520, the process 500 can include receiving an input power from a power source at block 522 and converting the input power to the supply power at block 524.

Figure 8:
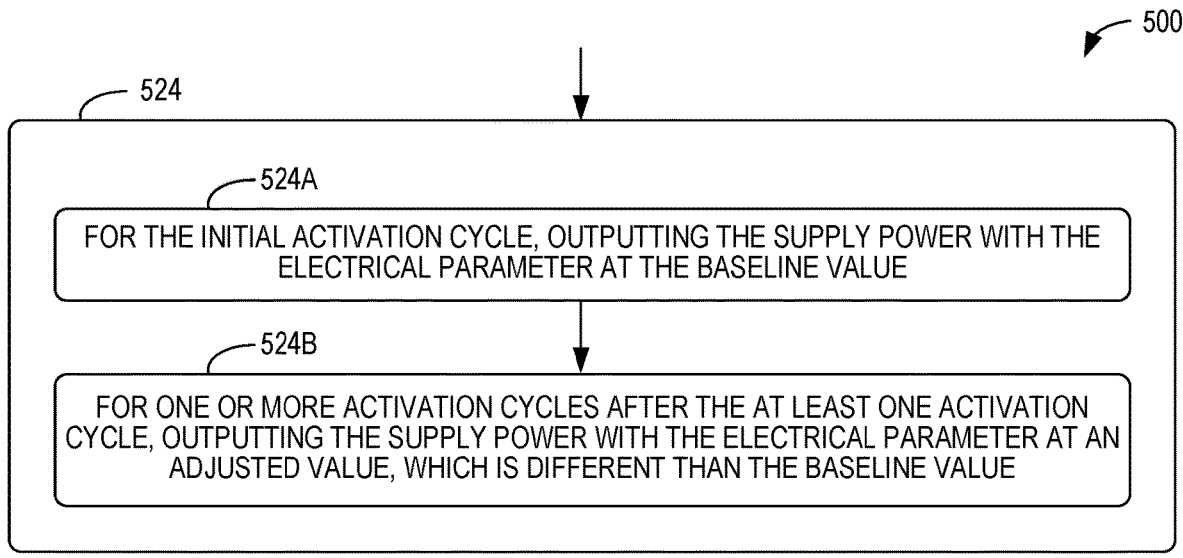
FIG. 8 illustrates a flow chart of an example process for operating a UV light source that can be used with the process shown in FIG. 7.

Also, as shown in FIG. 8, for the initial activation cycle, converting the input power to the supply power at block 524 can include outputting the supply power with the electrical parameter at the baseline value at block 524A and, for one or more activation cycles after the at least one activation cycle, converting the input power to the supply power at block 524 can include outputting the supply power with the electrical parameter at an adjusted value, which is different than the baseline value at block 524B.

Figure 9:
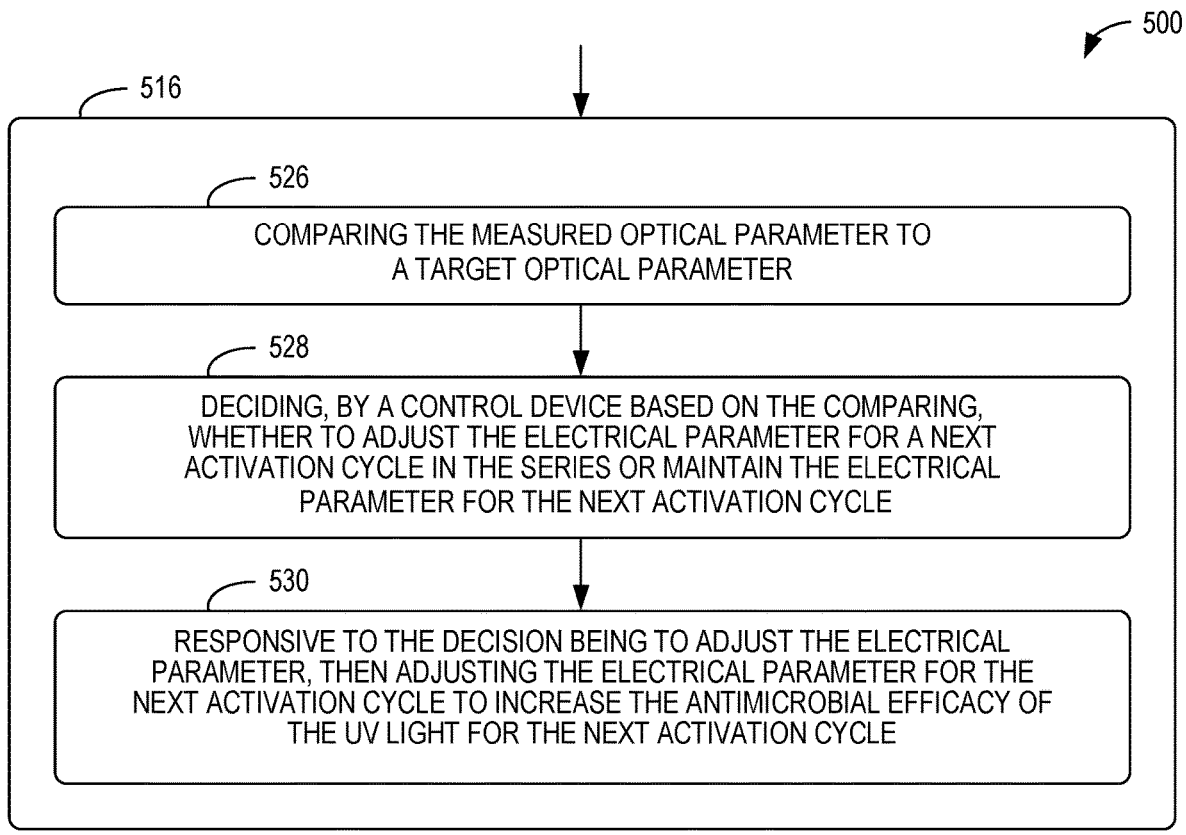
FIG. 9 illustrates a flow chart of an example process for operating a UV light source that can be used with the process shown in FIGS. 5-8.

As shown in FIG. 9, adjusting the electrical parameter at block 516 can include (i) comparing the measured optical parameter to a target optical parameter at block 526, (ii) deciding, by a control device based on the comparison at block 526, whether to adjust the electrical parameter for a next activation cycle in the series or maintain the electrical parameter for the next activation cycle at block 528, and (iii) responsive to the decision being to adjust the electrical parameter, then adjusting the electrical parameter for the next activation cycle to increase the antimicrobial efficacy of the UV light for the next activation cycle at block 530. The target optical parameter is related to the target antimicrobial efficacy of the UV light.

Figure 10:
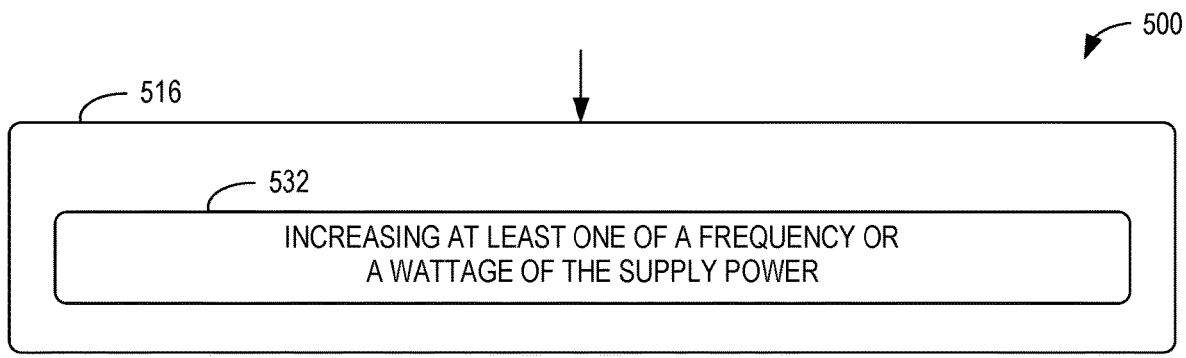
FIG. 10 illustrates a flow chart of an example process for operating a UV light source that can be used with the process shown in FIGS. 5-9.
Figure 11:
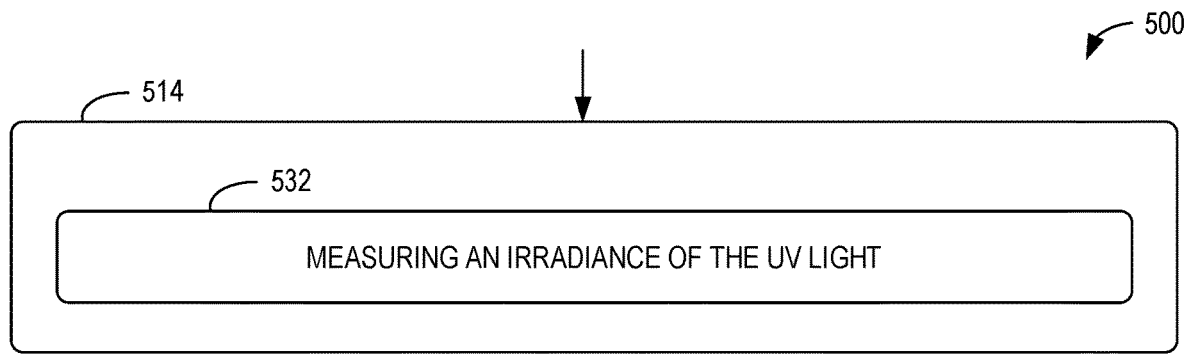
FIG. 11 illustrates a flow chart of an example process for operating a UV light source that can be used with the process shown in FIGS. 5-10.
Figure 12:
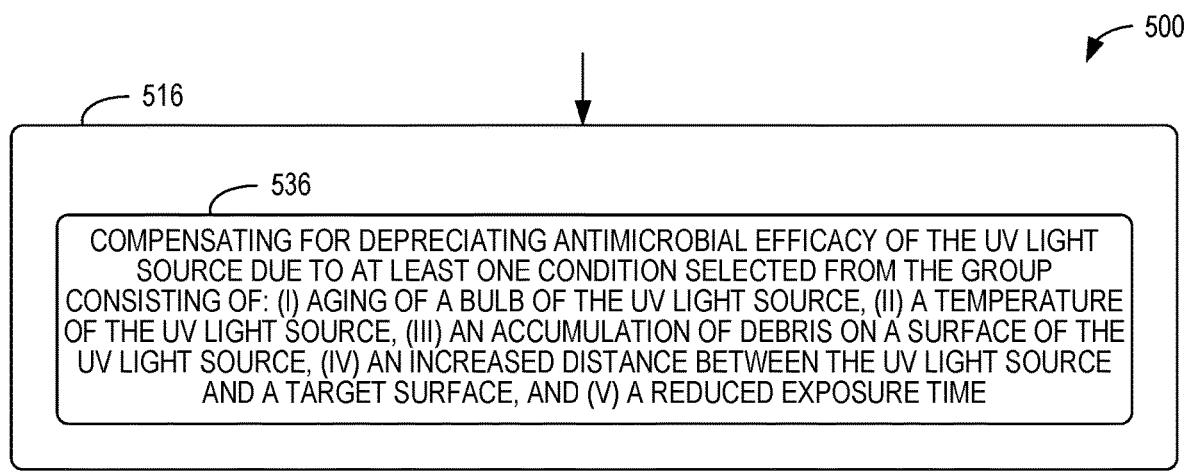
FIG. 12 illustrates a flow chart of an example process for operating a UV light source that can be used with the process shown in FIGS. 5-11.

As shown in FIG. 10, adjusting the electrical parameter at block 516 can include increasing at least one of a frequency or a wattage of the supply power at block 532. As shown in FIG. 11, sensing the UV light to measure the optical parameter at block 514 can include measuring an irradiance of the UV light at block 534. As shown in FIG. 12, adjusting the electrical parameter at block 516 can include compensating for depreciating antimicrobial efficacy of the UV light source due to at least one condition selected from the group consisting of: (i) aging of a bulb of the UV light source, (ii) a temperature of the UV light source, (iii) an accumulation of debris on a surface of the UV light source, (iv) an increased distance between the UV light source and a target surface, and/or (v) a reduced exposure time at block 536.

Figure 13:
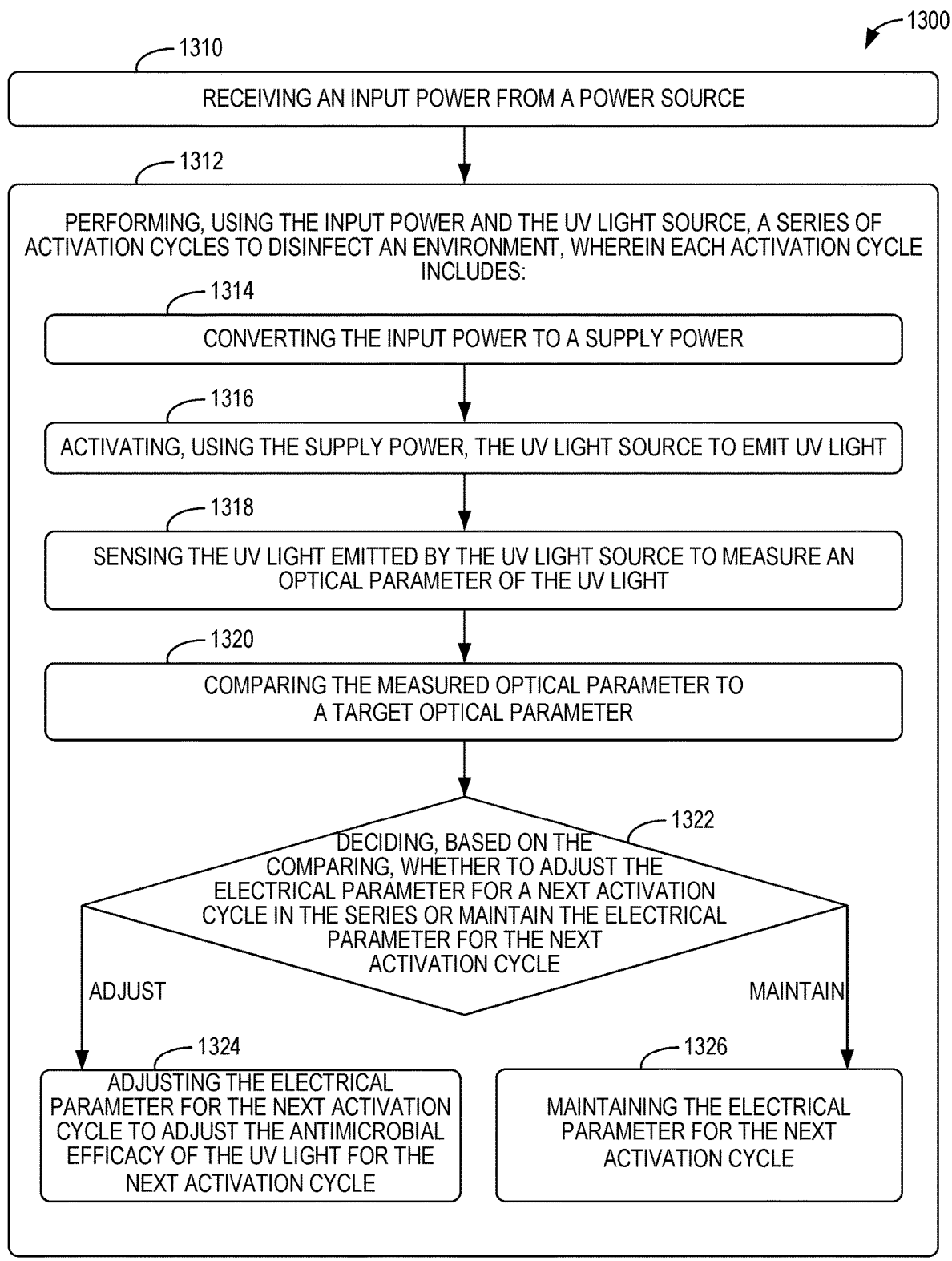
FIG. 13 illustrates a flow chart of an example process for operating a UV light source according to an example embodiment.

Referring now to FIG. 13, a flowchart for a process 1300 of operating a UV light source is illustrated according to an example embodiment. As shown in FIG. 13, at block 1310, the process 1300 includes receiving an input power from a power source. At block 1312, the process includes performing, using the input power and the UV light source, a series of activation cycles to disinfect an environment. Each activation cycle includes the operations of blocks 1314-1428.

At block 1314, the process 1300 includes converting the input power to a supply power. An electrical parameter of the supply power is adjustable, and the electrical parameter has a baseline value for an initial activation cycle in the series. At block 1316, the process 1300 includes activating, using the supply power, the UV light source to emit UV light. At block 1318, the process 1300 includes sensing the UV light emitted by the UV light source to measure an optical parameter of the UV light. At block 1320, the process 1300 includes comparing the measured optical parameter to a target optical parameter. The target optical parameter is related to a target antimicrobial efficacy of the UV light.

At block 1322, the process includes deciding, based on the comparison at block 1320, whether to adjust the electrical parameter for a next activation cycle in the series or maintain the electrical parameter for the next activation cycle. If the decision at block 1322 is to adjust the electrical parameter, then the process 1300 includes adjusting the electrical parameter for the next activation cycle to adjust the antimicrobial efficacy of the UV light for the next activation cycle at block 1324. If the decision is to maintain the electrical parameter at block 1322, then the process 1300 includes maintaining the electrical parameter for the next activation cycle at block 1326. For at least one activation cycle in the series, the decision is to adjust the electrical parameter at block 1324.

Figure 14:
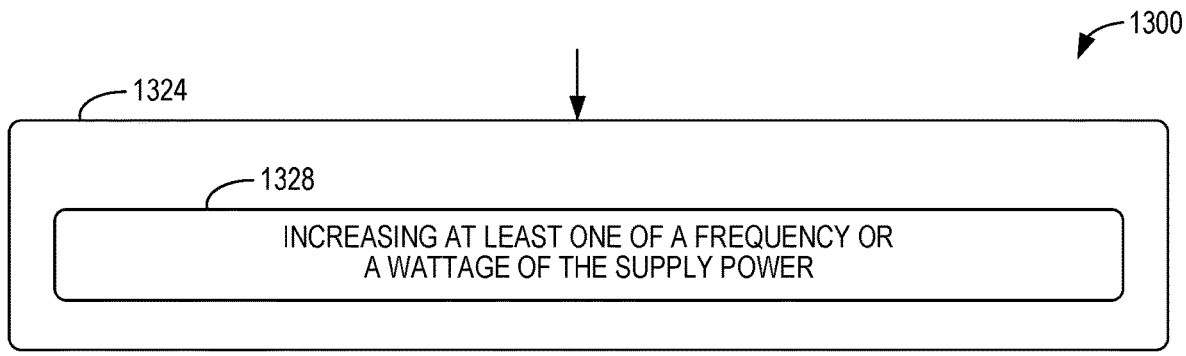
FIG. 14 illustrates a flow chart of an example process for operating a UV light source that can be used with the process shown in FIG. 13.
Figure 15:
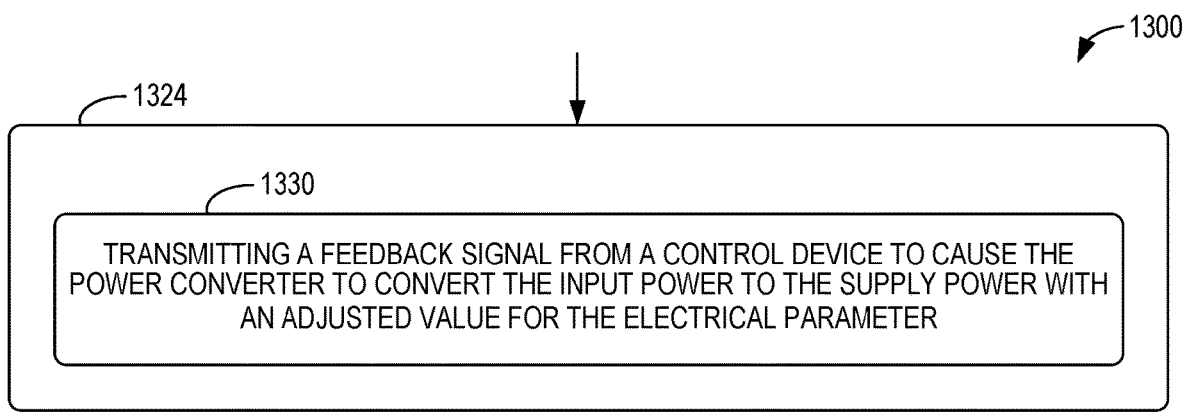
FIG. 15 illustrates a flow chart of an example process for operating a UV light source that can be used with the process shown in FIGS. 13-14.

FIGS. 14-15 depict additional aspects of the process 1300 according to further examples. In an example, the supply power is an AC power. In this example and as shown in FIG. 14, adjusting the value of the electrical parameter at block 1324 includes increasing at least one of a frequency or a wattage of the supply power at block 1328. Also, in an example, converting the input power to the supply power at block 1314 is performed by a power converter. In this example and as shown in FIG. 15, adjusting the electrical parameter at block 1324 includes transmitting a feedback signal from a control device to cause the power converter to convert the input power to the supply power with an adjusted value for the electrical parameter at block 1330.

Any of the blocks shown in FIGS. 5-15 may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In some instances, components of the devices and/or systems described herein may be configured to perform the functions such that the components are actually configured and structured (with hardware and/or software) to enable such performance. Example configurations then include one or more processors executing instructions to cause the system to perform the functions. Similarly, components of the devices and/or systems may be configured so as to be arranged or adapted to, capable of, or suited for performing the functions, such as when operated in a specific manner.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A method of operating an ultraviolet (UV) light source, comprising:
   detecting, using a triggers sensor, a trigger condition;
   responsive to detecting the trigger condition, generating a trigger-sensor signal indicating that the trigger condition was detected;
   determining, based on the trigger-sensor signal, that one or more criteria are met, wherein the one or more criteria includes a condition that an environment to be disinfected by the UV light source is unoccupied;
   responsive to determining that the one or more criteria are met, transmitting a control signal to cause the UV light source to emit UV light and disinfect at least a target surface in the environment; and
   providing a supply power to the UV light source;
   activating, using the supply power, the UV light source to emit UV light during a series of activation cycles, wherein each activation cycle is initiated in response to a respective transmission of the control signal;
   during at least one activation cycle in the series, sensing the UV light emitted by the UV light source to measure an irradiance of the UV light, wherein the irradiance is related to an antimicrobial efficacy of the UV light;
   performing a comparison, using the irradiance measured during the at least one activation cycle, of the antimicrobial efficacy of the UV light to a target level of antimicrobial efficacy to be maintained; and
   maintaining a target antimicrobial efficacy of the UV light over the series of activation cycles by controlling, based on the comparison, an intensity of the UV light source,
   wherein controlling the intensity of the UV light source comprises adjusting, based on the measured irradiance, an electrical parameter of the supply power to maintain the target antimicrobial efficacy of the UV light over the series of activation cycles, and
   wherein, for a given value of the electrical parameter, the intensity of the UV light emitted by the UV light source depreciates over the series of activation cycles.

2. The method of claim 1, wherein the trigger sensor comprises at least one sensor selected from a group consisting of: a motion sensor, an occupancy sensor, a thermal sensor, an open/close sensor, an infrared sensor device, and ultrasonic sensor device, and a floor pressure sensor.

3. The method of claim 2, wherein the trigger condition comprises at least one trigger condition selected from a group consisting of: a door of a lavatory being opened, a door of the lavatory being closed, the lavatory being occupied, and the lavatory being unoccupied.

4. The method of claim 1, wherein the one or more criteria is at least one criterion selected from a group consisting of: a door of a lavatory being closed, the lavatory being unoccupied, the lavatory having been occupied a predetermined number of times since a previous activation of the UV light source, and a predetermined amount of time having passed since the previous activation of the UV light source.

5. The method of claim 1, wherein activating the UV light source comprises emitting the UV light at a wavelength of approximately 222 nanometers.

6. The method of claim 1, wherein the UV light source is configured to emit the UV light in a range between a minimum intensity and a maximum intensity,
   wherein, for an initial activation cycle in the series, the electrical parameter has a baseline value that is configured such that activating the UV light source using the supply power comprises emitting the UV light at an intensity that (i) is less than the maximum intensity of the UV light source and (ii) provides the target antimicrobial efficacy.

7. The method of claim 6, further comprising:
for each activation cycle in the series:
receiving an input power from a power source; and
converting the input power to the supply power,
wherein, for the initial activation cycle, converting the input power to the supply power comprises outputting the supply power with the electrical parameter at the baseline value, and
wherein, for one or more additional activation cycles after the at least one activation cycle, converting the input power to the supply power comprises outputting the supply power with the electrical parameter at an adjusted value, which is different than the baseline value.

8. The method of claim 1, wherein adjusting the electrical parameter comprises:
comparing the measured irradiance to a target optical parameter, wherein the target optical parameter is related to the target antimicrobial efficacy of the UV light;
deciding, by a control device based on the comparing, whether to adjust the electrical parameter for a next activation cycle in the series or maintain the electrical parameter for the next activation cycle; and
responsive to the decision being to adjust the electrical parameter, then adjusting the electrical parameter for the next activation cycle to increase the antimicrobial efficacy of the UV light for the next activation cycle.

9. The method of claim 1, wherein the supply power is an alternating current (AC) power, and
wherein adjusting the electrical parameter comprises increasing at least one of a frequency or a wattage of the supply power.

10. A light control system, comprising:
a power converter configured to convert an input power received from a power source to a supply power;
an ultraviolet (UV) light source configured to receive the supply power and emit UV light;
a trigger sensor configured to detect a trigger condition and, responsive to detecting the trigger condition, generate a trigger-sensor signal indicating that the trigger condition was detected;
a control device communicatively coupled to the power converter and the trigger sensor, wherein the control device is configured to:
determine, based on the trigger-sensor signal, that one or more criteria are met, wherein the one or more criteria includes a condition that an environment to be disinfected by the UV light source is unoccupied; and
responsive to determining that the one or more criteria are met, transmit a control signal to cause the UV light source to emit the UV light and disinfect at least a target surface in the environment; and
a light sensor configured to measure an irradiance of the UV light emitted by the UV light source,
wherein the irradiance is related to an antimicrobial efficacy of the UV light,
wherein the supply power has an electrical parameter that is adjustable by the power converter,
wherein the UV light source is configured to receive the supply power and emit the UV light during a series of activation cycles,
wherein an intensity of the UV light emitted by the UV light source is based, at least in part, on the electrical parameter of the supply power, and
wherein the control device is further configured to maintain a target antimicrobial efficacy of the UV light over the series of activation cycles by iteratively performing a plurality of acts comprising:
receiving, from the light sensor, a sensor signal indicating the irradiance measured by the light sensor,
performing a comparison of the irradiance indicated by the sensor signal to a target optical parameter, wherein the target optical parameter is related to the target antimicrobial efficacy, and
based on the comparison, providing a feedback signal to the power converter to cause the power converter to adjust the electrical parameter of the supply power for a next activation cycle in the series.

11. The system of claim 10, wherein the trigger sensor comprises at least one sensor selected from a group consisting of: a motion sensor, an occupancy sensor, a thermal sensor, an open/close sensor, an infrared sensor device, and ultrasonic sensor device, and a floor pressure sensor.

12. The system of claim 11, wherein the trigger condition comprises at least one trigger condition selected from a group consisting of: a door of a lavatory being opened, a door of the lavatory being closed, the lavatory being occupied, and the lavatory being unoccupied.

13. The system of claim 10, wherein the one or more criteria is at least one criterion selected from a group consisting of: a door of a lavatory being closed, the lavatory being unoccupied, the lavatory having been occupied a predetermined number of times since a previous activation of the UV light source, and a predetermined amount of time having passed since the previous activation of the UV light source.

14. The system of claim 10, wherein the UV light source is configured to emit the UV light at a wavelength of approximately 222 nanometers.

15. The system of claim 10, wherein the supply power is an alternating current (AC) power, and
wherein the electrical parameter is at least one of a frequency or a wattage of the supply power.

16. The system of claim 10, wherein the UV light source comprises:
a housing comprising:
a first side-wall,
a second side-wall,
a top wall extending between the first side-wall and the second side-wall,
a first end wall extending between the first side-wall, the second side-wall, and the top wall, and
a second end wall extending between the first side-wall, the second side-wall, and the top wall,
wherein the first side-wall, the second side-wall, the top wall, the first end wall, and the second end wall define an interior space; and
a lamp that is coupled to the first end wall and the second end wall in the interior space of the housing.

17. The system of claim 10, wherein the UV light source is in on an aircraft.

18. The system of claim 10, wherein the UV light source is in a lavatory of an aircraft.

19. The system of claim 16, wherein the light sensor is in the interior space of the housing.

20. The system of claim 19, wherein the light source is coupled to the top wall in the interior space of the housing.

* * * * *